(12) United States Patent
Granger et al.

(10) Patent No.: US 9,486,551 B2
(45) Date of Patent: Nov. 8, 2016

(54) AIR FRESHENER SYSTEM

(71) Applicant: Momentum Industries, Inc., Rome City, IN (US)

(72) Inventors: David A. Granger, Syracuse, IN (US); Terry L. Hygema, Greer, SC (US)

(73) Assignee: Momentum Industries, Inc., Rome City, IN (US)

( * ) Notice: Subject to any disclaimer, the term of this patent is extended or adjusted under 35 U.S.C. 154(b) by 206 days.

(21) Appl. No.: 14/031,786

(22) Filed: Sep. 19, 2013

(65) Prior Publication Data

US 2014/0076989 A1    Mar. 20, 2014

Related U.S. Application Data

(60) Provisional application No. 61/702,877, filed on Sep. 19, 2012.

(51) Int. Cl.

| | | |
|---|---|---|
| *A24F 25/00* | (2006.01) | |
| *A61L 9/04* | (2006.01) | |
| *A61L 9/12* | (2006.01) | |
| *A47K 10/16* | (2006.01) | |
| *A47K 10/32* | (2006.01) | |

(52) U.S. Cl.
CPC ............... *A61L 9/12* (2013.01); *A47K 10/16* (2013.01); *A47K 2010/322* (2013.01)

(58) Field of Classification Search
CPC ... A61L 9/12; A47K 10/16; A47K 2010/322
USPC ...................................... 239/34–60
See application file for complete search history.

(56) References Cited

U.S. PATENT DOCUMENTS

| | | | | |
|---|---|---|---|---|
| 3,771,883 A | * | 11/1973 | Terepin ............... | A47K 10/32 242/160.1 |
| 5,170,938 A | * | 12/1992 | Dewing ............... | A47K 10/32 239/34 |
| 5,341,992 A | * | 8/1994 | Bishopp .............. | A47K 10/38 239/34 |
| 2004/0188535 A1 | * | 9/2004 | Hart .................... | A61L 9/12 239/57 |
| 2005/0224594 A1 | * | 10/2005 | Wolf ................... | A61L 9/12 239/34 |

* cited by examiner

*Primary Examiner* — Justin Jonaitis
(74) *Attorney, Agent, or Firm* — Taylor IP, P.C.

(57) ABSTRACT

An air freshener system includes a roll paper assembly and an air freshener assembly coupled with the roll paper assembly. The air freshener assembly includes an integrated air freshener element in the form of a single, continuous gel component.

12 Claims, 7 Drawing Sheets

AIR FRESHENER SYSTEM

CROSS REFERENCE TO RELATED APPLICATIONS

This is a non-provisional application based upon U.S. Provisional Patent Application Ser. No. 61/702,877, entitled "AIR FRESHENER", filed Sep. 19, 2012, which is incorporated herein by reference.

BACKGROUND OF THE INVENTION

1. Field of the Invention

The present invention relates to an air freshener system.

2. Description of the Related Art

A number of mechanisms are known in the art for odor elimination and fragrance release both indoors and outdoors. For example, aerosol sprays having a variety of fragrances have been known in the art for a long time. Aerosol sprays can, however, leave a sticky residue on the surface of the area over which they are sprayed. Carpet powders are also known which are sprinkled over a predefined area and, after setting for a period of time, are cleaned with a vacuum to remove powder particulate from the area. Depending upon the suction power and filter of the vacuum utilized, however, a layer of fine powder may remain which can be easily sent airborne by normal movement about the area. This can negatively affect, for example, individuals with compromised respiratory systems.

Candles have also been utilized to cover undesirable odors and release fragrance over a selected area. The attendant risk with candles, however, is the risk of fire, as well as the risk of injury to individuals, particularly young children who may not understand the risk of burns associated with fire. Candles also have a tendency to smoke when the wicks become too long and, thus, leave behind an undesirable fine black residue on nearby surfaces.

Another method for elimination of undesirable odors, is to provide a plurality of small beads, coated with layer of scented oil in a vented container. The problem with this type of odor eliminator, however, is that if spilled, the oil is messy and difficult to clean. Further, if the small, oil covered beads were to be spilled, they would be difficult to collect and would result in a slip and fall risk, which could result in personal injury.

What is needed in the art is an effective, compact and safe system for elimination of undesirable odors and/or fragrance distribution which avoids the problems of the known art.

SUMMARY OF THE INVENTION

The present invention provides an air freshener system including a roll paper assembly and an air freshener assembly coupled with the roll paper assembly. The air freshener assembly includes an integrated air freshener element in the form of a single, continuous gel component, for example in the form of a gel ring or disc.

The invention in another form is directed to an air freshener system including an inner cage having a tray coupled with a neck formed as a substantially cylindrical element for positioning within a longitudinal end of a roll core of a paper roll, for example a paper towel roll or a toilet paper roll. The inner cage is coupled with a cover to form an inner well therebetween. A single, continuous gel component formed as a gel ring is positioned within the well between the inner cage and the cover.

The invention in yet another form is directed to an air freshener system including at least one side section, at least one air freshener element in the form of a single, continuous gel component, and a main section which is pivotally coupled with the at least one side section. The main section is configured for receiving the air freshener element and the air freshener element, the main section and the at least one side section lie substantially flat against each other in a closed position.

Advantageously, an air freshener assembly as discussed above can be attached to at least one of a pair of longitudinal ends of any of a number of rolled paper products, for example paper towels, toilet paper, etc., they can effectively capture the paper therebetween and hold the paper so that it does not shift, for example horizontally.

Further, the gel used as part of the fragrance/absorbent assembly can include an odor emitting fragrance or an odor absorbent material (or the odor absorbent material can be a different substance altogether). Thus, the fragrance/absorbent assembly can cover up and/or eliminate unpleasant odors and/or produce a pleasant fragrance. The fragrance/absorbent assembly can be used in a number of different places; by way of example, and not by limitation, such places include the kitchen, bathroom, garage, utility room, baby room, pet area, garbage area, and anywhere rolled paper goods are used. Since an air freshener assembly as inventively defined herein can be inserted into each longitudinal end of a rolled.

Advantageously, the air freshener system according to the present invention holds gel fragrance in a simple snap-together package. Further, as the rolled paper product is used and unwound, vents draw air in and around the gel to produce air circulation, thereby emitting fragrance and/or absorbing unpleasant odors. This increases gel life since the fragrance/absorbent is primarily emitted during use, for example during rotation of the gel, which creates air circulation.

Another advantage is that the air freshener system of the present invention provides for easy use. For example, the neck of the inner cage of the air freshener system according to one embodiment of the present invention slides into an end of rolled paper good products. Further, the foldable air freshener system allows for easy use due to its pivotally coupled opposing side and central section, each of which may have an air freshener element.

Yet another advantage is air freshener systems according to the present invention provide a low cost, simple design which is aesthetically appealing and functional. Any aesthetically pleasing design can, for example, be incorporated into the air freshener system according to the present invention. Accordingly, the present invention can be designed to match a number of decors.

The invention in yet another form is directed to an air freshener system including a pair of opposing side sections, at least one air freshener element in the form of a single, continuous gel component, and a center section which is positioned between and pivotally coupled with the opposing side sections. The center section is configured for receiving the air freshener element and the air freshener element, the center section and the opposing side sections lie substantially flat against each other in a closed or folded position.

Advantageously, the folding air freshener system allows for either one of or both sides of the system to be open. Further, different fragrances could be used on each side, thereby creating unique scent combinations.

The folding air freshener system described herein can further be hung to mitigate unit abuse, for example children playing with the folding assembly.

Additional aesthetic options are also available via the folding air freshener system according to the present inventions. More specifically, slide in pictures in the form of inserts may be provided to match with different decors. Further, different styles of air freshener element retainers may be provided to capture the spirit of different holidays, seasons or moods.

An additional advantage of the folding air freshener system according to the present invention is that since it is foldable and may, therefore, be put into a compact configuration, packaging may be accomplished at lower cost and space may be saved in storing the system.

Yet another advantage of the folding air freshener system according to the present invention is that the system may be closed to preserve the fragrance, for example at night or when otherwise not needed.

Further, differently shaped air freshener elements may be provided, for example, snowflake shaped, heart shaped, etc. to reflect to the character of the scent itself or for purely aesthetic purposes.

BRIEF DESCRIPTION OF THE DRAWINGS

The above-mentioned and other features and advantages of this invention, and the manner of attaining them, will become more apparent and the invention will be better understood by reference to the following description of embodiments of the invention taken in conjunction with the accompanying drawings, wherein.

Corresponding reference characters indicate corresponding parts throughout the several views. The exemplifications set out herein illustrate embodiments of the invention and such exemplifications are not to be construed as limiting the scope of the invention in any manner.

DETAILED DESCRIPTION OF THE INVENTION

Figure 1:
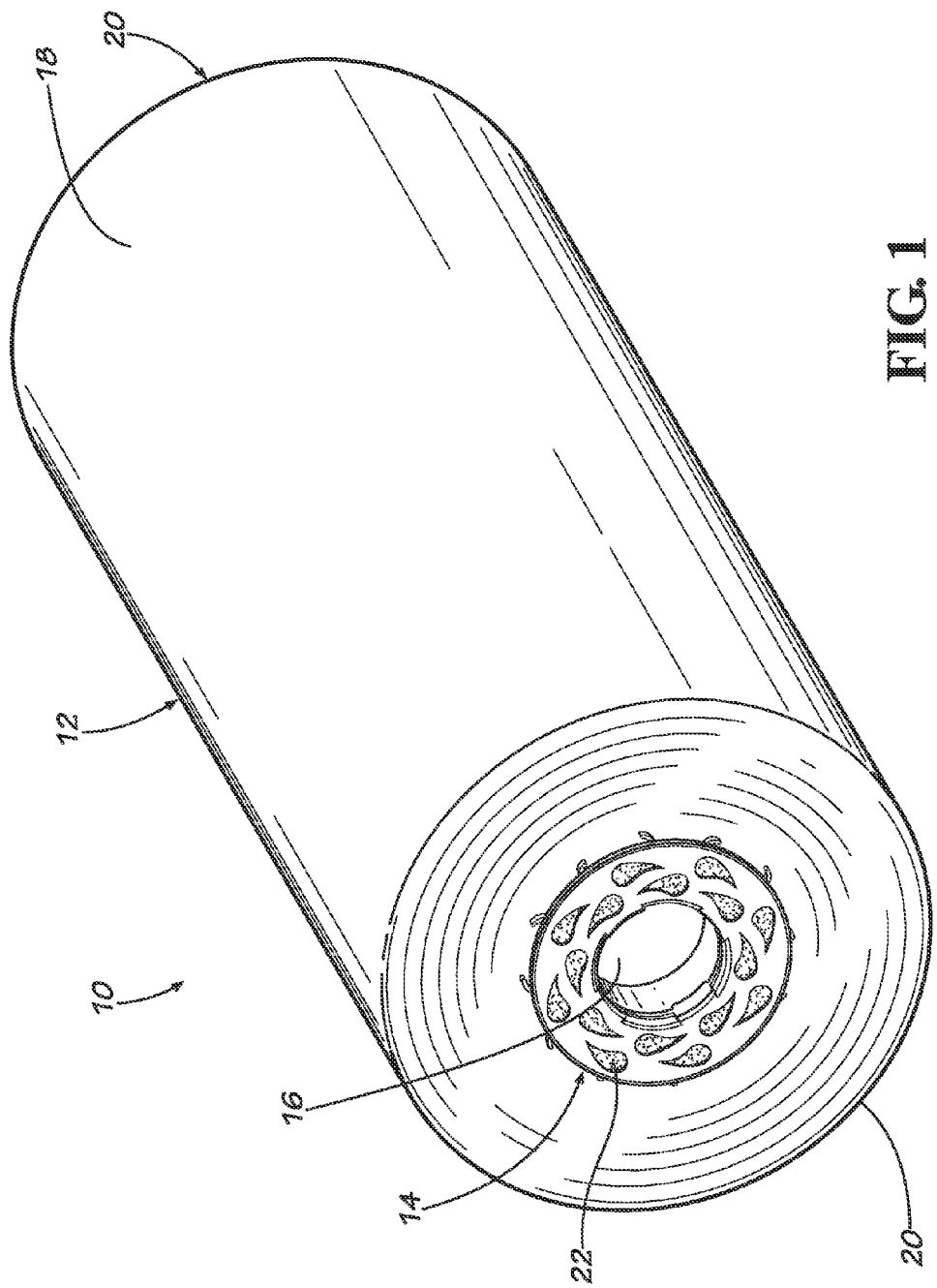
FIG. 1 is a perspective view of an air freshener system according to the present invention.

Referring now to the drawings, and more particularly to FIGS. 1-4, there is shown an air freshener system 10 which generally includes a roll paper assembly 12 and at least one air freshener assembly 14.

Roll paper assembly 12 includes a roll core 16 and paper 18 rolled on roll core 16, as illustrated in FIG. 1. Roll core 16 has a pair of opposing longitudinal ends 20 and can be made, for example, of cardboard. Roll core 16 is typically a tubular element around which roll paper 18 is rolled (or, more generally, wrapped). Roll paper assembly 12 is for example, a toilet paper roll or a paper towel wrapper.

The air freshener assembly 14 is slid into one longitudinal end of roll core 16 until air freshener assembly 14 abuts that end 20 of roll core 16, the air freshener assembly 14 thereby forming an interference fit with roll core 16. As set forth above, an additional air freshener assembly 14 (which can be substantially identical to the one inserted onto the opposing end 20 of roll core 16) can be slide onto the opposite longitudinal end of roll core 16 and attached thereto. FIG. 1 illustrates a single air freshener assembly 14 secured to one longitudinal end 20 of roll paper assembly 12 to form, at least in part, air freshener system 10.

Figure 2:
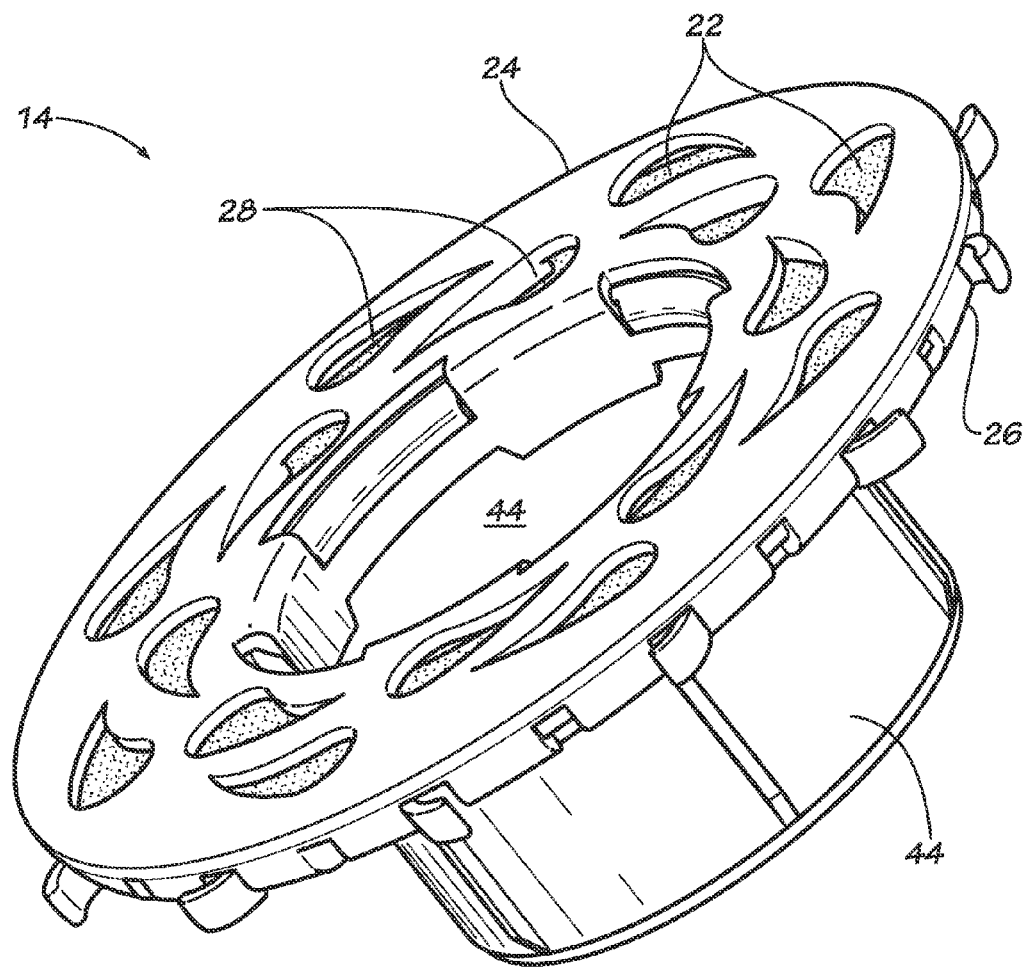
FIG. 2 is a perspective view of the air freshener assembly of the air freshener system illustrated in FIG. 1.
Figure 3:
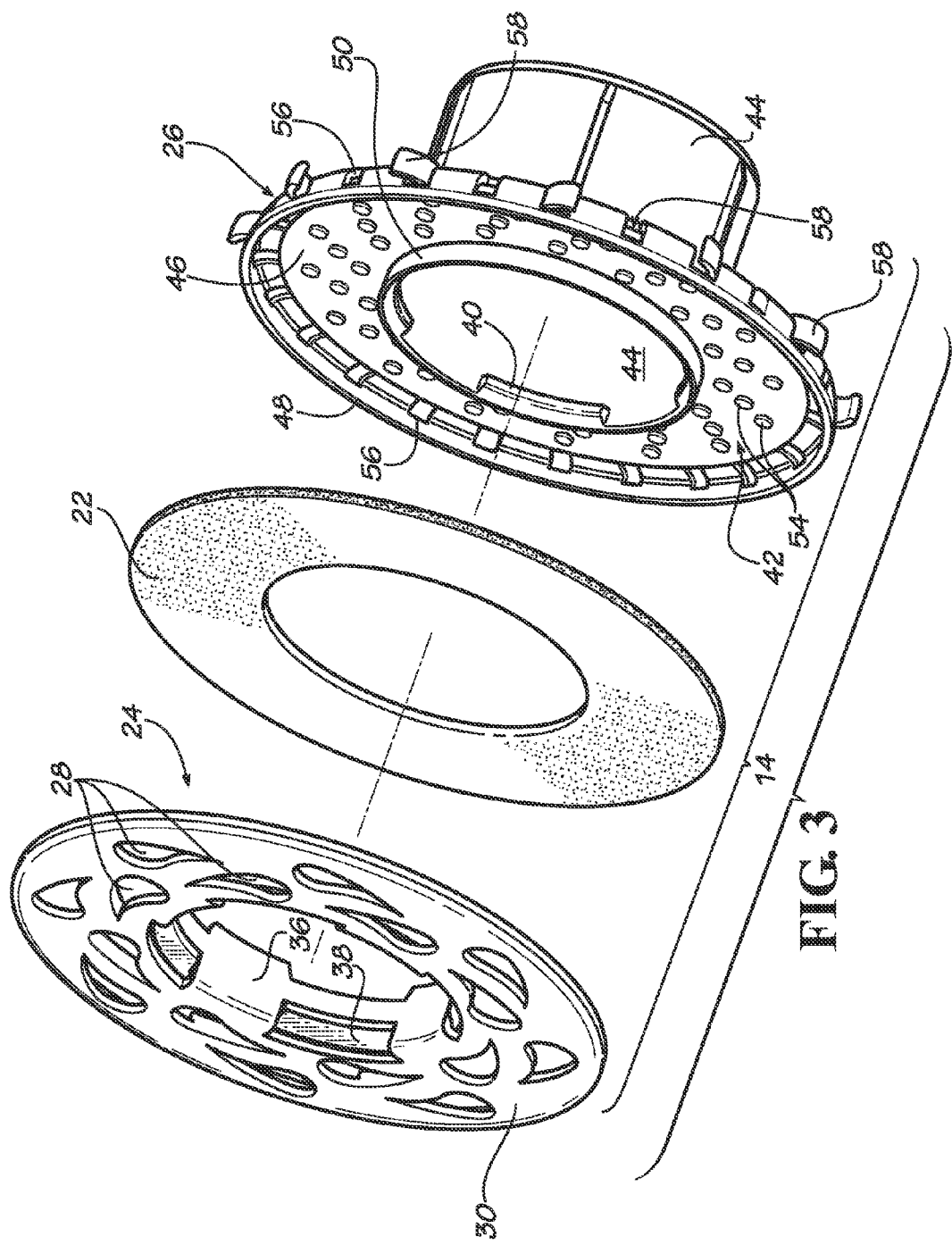
FIG. 3 is an exploded view of the air freshener assembly illustrated in FIGS. 1 and 2.

Referring now to FIGS. 2 and 3, there is shown air freshener assembly 14 including an integrated air freshener element 22, in the form of a single, continuous gel component, for example a gel ring or a gel disc. Air freshener system 10 can include more than one air freshener assembly 14, for example two air freshener assemblies 14, one being positioned at each longitudinal end 20 of roll core 16. Air freshener assembly 14 further includes a cover 24 coupled with an inner cage 26, between which air freshener element 22 is positioned.

Air freshener element 22 can be a fragrance element and/or an odor absorbing element. As a fragrance element, the air freshener element 22 can emit a fragrance into the surrounding air, especially when air flows across and/or through the fragrance element. Such a fragrance element is, for example, and not by limitation, a fragrance gel that is housed within a gel packet (the gel can emit a volatized chemical into the air, that is, a chemical in the gel can become volatile and can thereby pass off as a vapor from the packet). As an absorbent element, the air freshener element 22 can include odor absorbent material (such as a gel, but other substances could be used as well) which absorbs odor from the surrounding air. The air freshener element 22 can thereby cover up and/or eliminate unpleasant odors and/or produce a pleasant fragrance.

Figure 4:
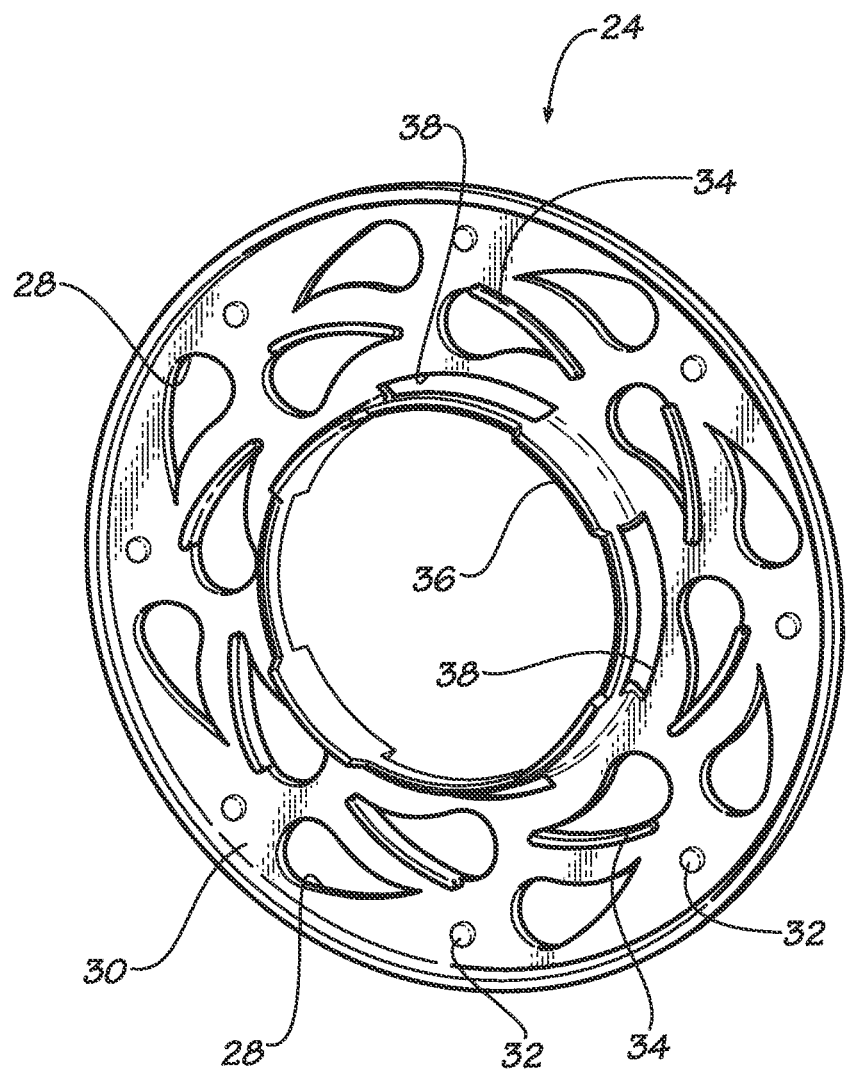
FIG. 4 is a bottom view of the cover of the air freshener assembly of FIGS. 1-3.

Cover 24, as illustrated in FIGS. 1-4, includes a plurality of vents 28 formed as through-holes through a base wall 30 of cover 24. In FIGS. 1-4, vents 28 are shown as being generally tear-drop shaped, but it is understood that other vent shapes can be used in addition to or instead of these tear-drop shaped vents. Vents 28 are configured to allow air to flow across and/or through the air freshener element 22. Referring now to FIG. 4, cover 24 also includes a plurality of pegs 32 and spacing walls 34 projecting in a direction towards air freshener element 22 and inner cage 26. Pegs 32 and spacing walls 34 serve to space air freshener element 22 apart from the base wall 30 of cover 24, at least in part. In this way, air can circulate between air freshener element 22 and base wall 30 of cover 24, enabling air freshener element 22 to function more efficiently. Cover 24 further includes an inner wall 36 on an inner radius of base wall 30. Inner wall 36 together with base wall 30 define a plurality of openings 38 which correspond with locking projections 40 of inner cage 26 to form a snap fit between cover 24 and inner cage 26.

Inner cage 26 includes a tray 42 and a neck 44 attached to tray 42. Tray 42 includes a base wall 46, an outer upstanding wall 48 and an inner upstanding wall 50, which form a well 52 into which air freshener element 22 is positioned. Locking projections 40 of inner cage 26 can be considered to be formed by inner upstanding wall 50 of tray 42. Locking projections 40 project radially inwardly from inner upstanding wall 50 (or, alternatively, can be positioned further from the free end of this upstanding wall 50 and, thus, be considered to be part of neck 44). Locking projections seat within radially inner openings 38 of cover 24 so as to snap-fit cover 24 to inner cage 26 and thereby capture air freshener element 22 between inner cage 26 and cover 24.

Neck 44 is formed as a substantially cylindrical element configured for positioning within roll core 16 or, more specifically, within at least one longitudinal end 20 of roll core 16. The outer upstanding wall 48 of tray 42 is positioned radially outwardly of an outer radius of air freshener element 22 and, at least in part, circumferentially surrounds the outer radius of the air freshener element 22. The inner upstanding wall 50 of tray 42 is positioned radially inwardly of an inner radius of air freshener element 22. Tray 42 further includes a plurality of pegs 54 positioned on base wall 46 and project in a direction towards air freshener element 22 and cover 24. Pegs 54 serve to space air freshener element 22 from base wall 46 of tray 42, at least in part. In this way, air can circulate between air freshener element 22 and base wall 46 of tray 42, enabling the air freshener element 22 to function more efficiently. Tray 42 further defines a plurality of vents 56 near an outer radius of the tray. Vents 56 are configured to allow air to circulate within inner cage 26 and cover 24 and to pass over and/or through air freshener element 22 so that the air freshener element functions more efficiently.

As set forth more fully above, neck 44 of inner cage 26 forms a generally cylindrical element which is positioned radially inwardly of roll core 16 of roll paper assembly 12. Neck 44 includes a plurality of axially extending runners 60 positioned on a radial outer surface of neck 44 (the surface which faces the inner radius of the roll core). Each of the runners 60 has a slanted portion to facilitate neck 44 being inserted into the interior of roll core 16.

Tray 42 further includes a plurality of barbs 58 spaced circumferentially about the tray 42 and generally projecting radially outwardly and also curving in a clockwise or a counter-clockwise direction. Some barbs 58 are curved in a clockwise direction, while others are curved in a counter-clockwise direction. The curvature of the barbs 58 serve to funnel or direct air to air freshener element 22 during rotation of roll paper assembly 12. If the roll paper assembly is rotated in a counter-clockwise direction, then the barbs curved in a counter-clockwise direction can be the primary barbs which direct the air to air freshener element 22. Conversely, if the roll paper assembly 12 is rotated in a clockwise direction, then the barbs curved in a clockwise direction can be the primary barbs which direct air to the air freshener element 22.

Air freshener assembly 14 is formed such that it may be removably coupled with longitudinal end 20 of roll core 16 by forming an interference fit with longitudinal end 20 of roll core 16. In other words, air freshener assembly 14 is slid into one longitudinal end 20 of roll core 16 until the air freshener assembly 14 abuts that end 20 of roll core 16, the air freshener assembly thereby forming an interference fit with roll core 16. As indicated above, another air freshener assembly, which can be substantially identical to the first air freshener assembly can be affixed to the opposing end 20 of roll core 16.

The inner cage 26 and cover 24 can be formed, for example (and not by way of limitation), by a molding operation. For example, the inner cage and the cover can be made of a polymeric material, such as a thermoplastic polymer or a thermoset polymer, and can be formed by injection molding or reaction injection molding. Alternatively, the inner cage and the cover may be made of a metallic or wood material.

During assembly, air freshener element 22 is positioned in the tray 42 of inner cage 26. Then, cover 24 can be snapped to inner cage 26 by way of the locking projections 40 on inner cage 26 and the openings 28 of the cover, thereby capturing air freshener element 22 between the inner cage 26 and cover 24. The neck 44 is then slid into the interior of roll core 16, the being sized such that it (particularly the runners on the neck) form a snug fit with the interior surface of roll core 16. The rotation of the rolled paper air freshener system during use causes air to flow through the vent 28, 56 of the assembly and thereby to release fragrance or to absorb odor.

Figure 5:
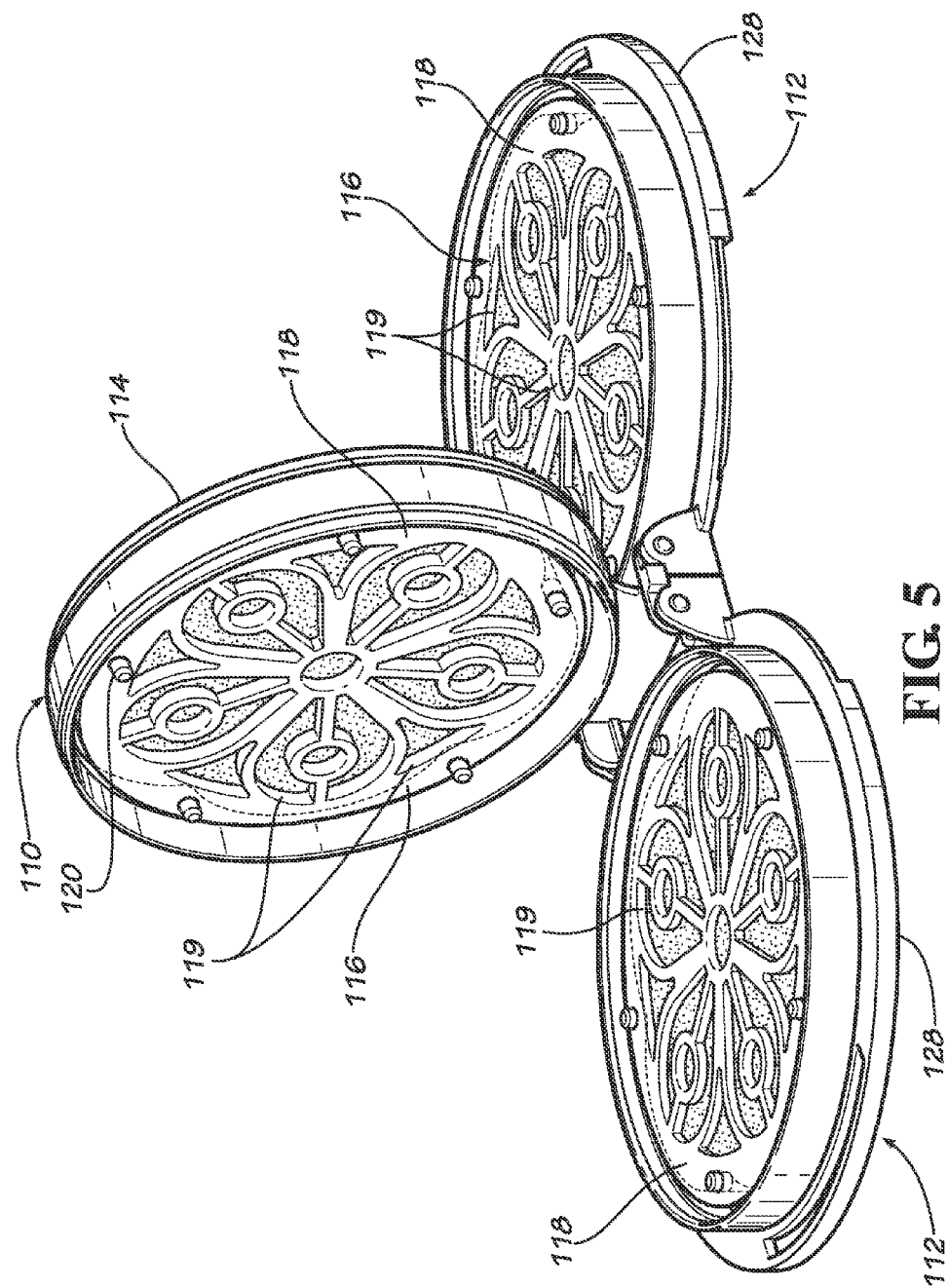
FIG. 5 is a perspective view of another embodiment of an air freshener system according to the present invention in the fully open position.
Figure 6:
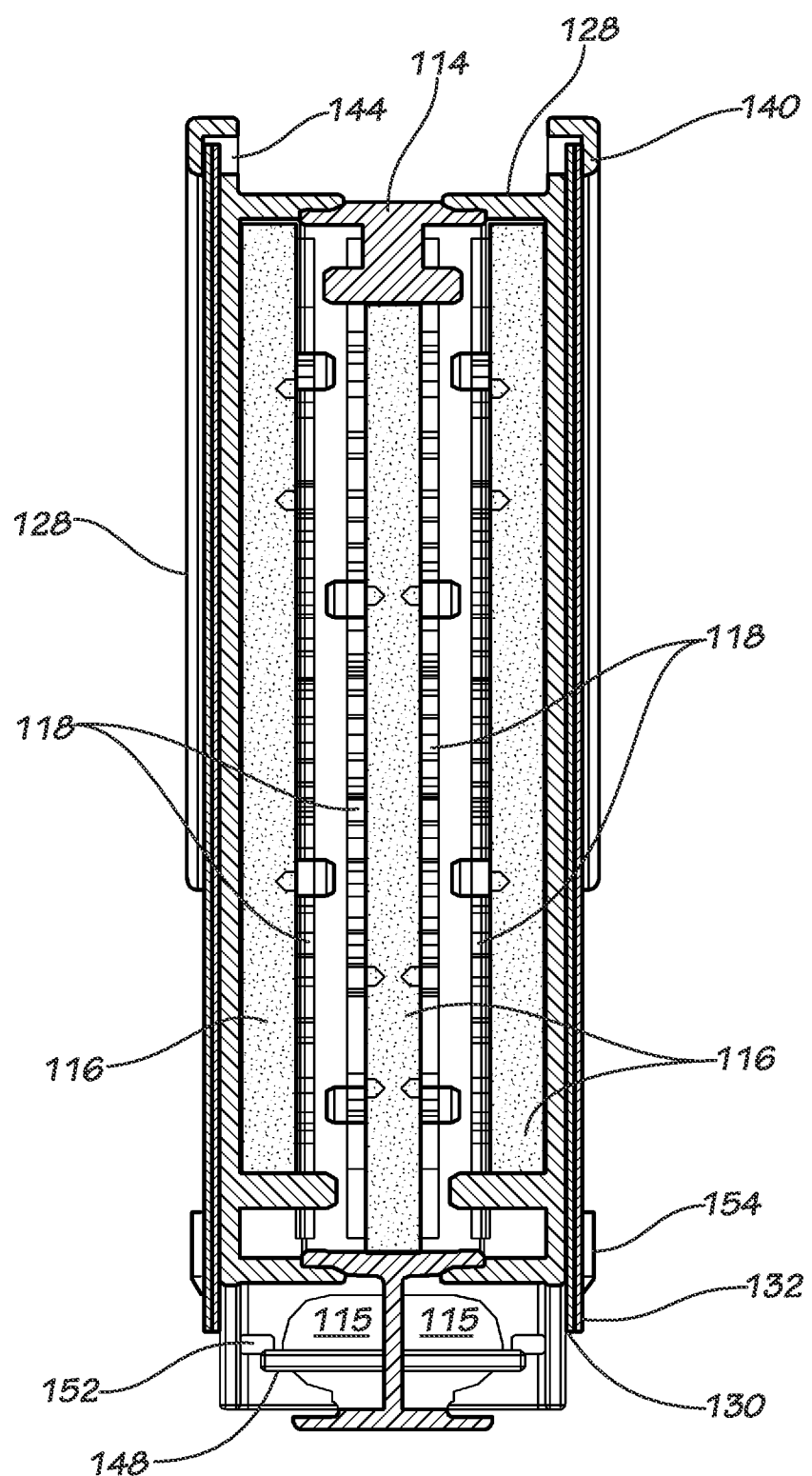
FIG. 6 is a perspective view of the air freshener system of FIG. 5 in a fully closed position.
Figure 7:
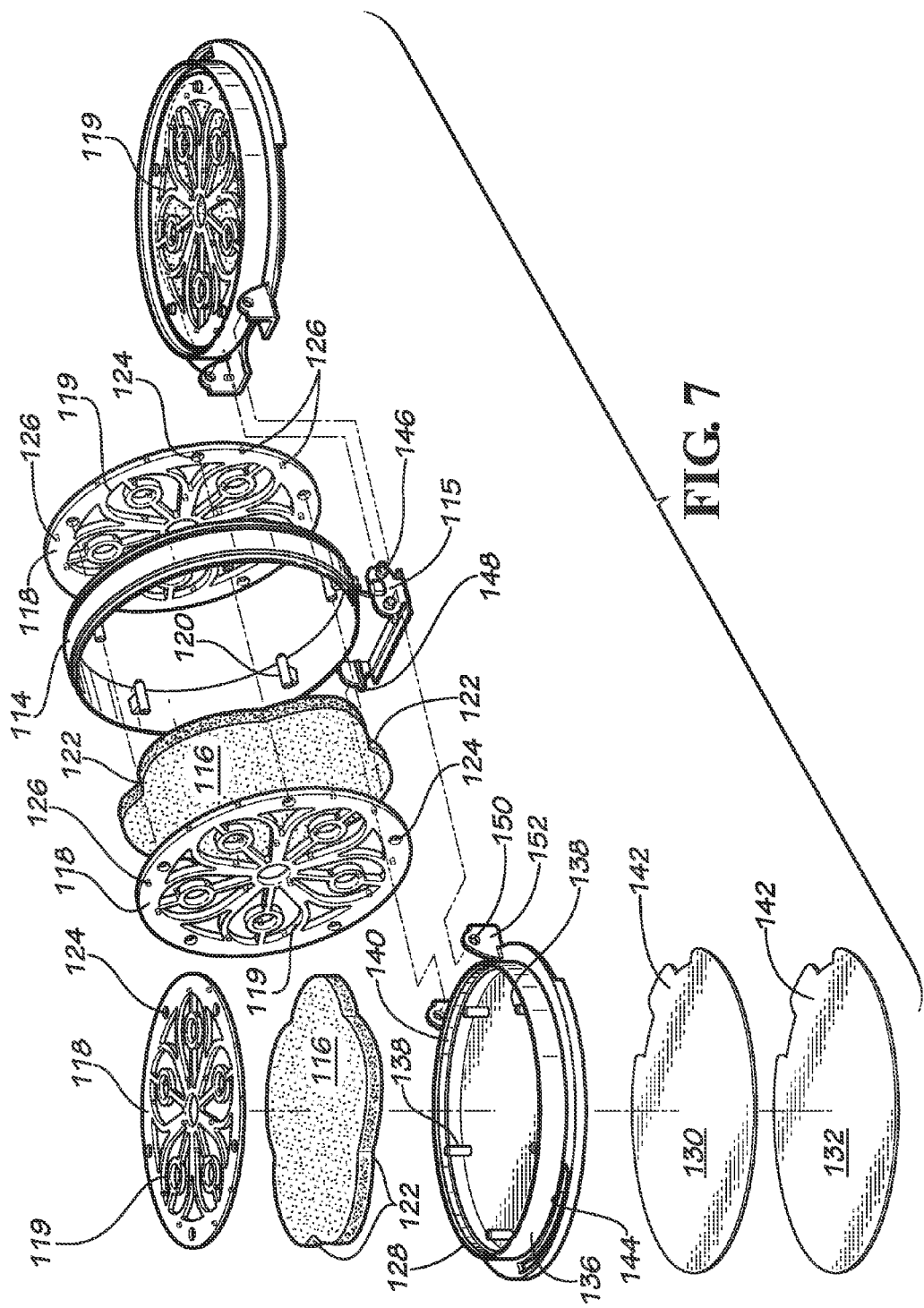
FIG. 7 is a partially exploded view of the air freshener system of FIGS. 5 and 6.

Referring now to FIGS. 5-7, there is shown an additional inventive embodiment of the air freshener system 100 generally including a center section 110 (which can also be referred to as a main section), a pair of opposing side sections 112, and at least one air freshener element 114. Each side section 112 is substantially identical to each other. Thus, a description of one side section serves as a description of the other side section. For purposes of discussion, each of the side sections illustrated in FIG. 5-7 are referred to herein as the side section (unless otherwise specifically referred to as the left or right side section). While the air freshener system 100 is shown as including two opposing side sections 112, it should be appreciated that the air freshener system 100 could also include only one side section 112 pivotally coupled to the main section 110.

FIG. 5 illustrates air freshener system 100, which can be referred to as a foldable air freshener system, pivoted to a fully open position. Alternatively, air freshener system 100 can be pivoted to a partially open position with one side section 112 pivoted an open position and the opposing side section 112 lying flat against center section 110. Additionally, air freshener system 100 can be fully closed (as seen in FIG. 6) with each of the opposing side sections 112 lying flat against center section 110. Further, FIG. 7 is a partially exploded view of the air freshener system 100 of FIGS. 5 and 6.

Referring specifically now to FIGS. 5 and 7, there is shown air freshener system 100 including center section 110 and two opposing side sections 112. Center section 110 includes a base 114, an air freshener element 116 and two retainer elements 118 (only one of which is visible in FIG. 5) which sandwich air freshener element 116 therebetween. Base 114 of center section 110 includes a plurality of axially extending prongs 120 which are positioned radially inwardly of the inner circumferential surface of base 114. Air freshener element 116 is shaped to include a plurality of valleys 122 (as seen in FIG. 7) on the circumference of air freshener element 116. The air freshener element 116 is inserted axially into the center of base 114 and prongs 120 of base 114 are positioned in corresponding valleys 122 of air freshener element 116. Retainer elements 118 of center section 110 are inserted axially into the center of base 114 on either side of air freshener element 116. Each retainer element 118 includes a plurality of circumferentially spaced mounting through-holes 124. Retainer elements 118 mount to base 114 by way of prongs 120 and mounting through-holes 124. Thus, retainer elements 118 of center section 110 may be snapped onto prongs 120 using an interference fit so retainer elements 118 fit snugly onto prongs 120 and capture air freshener element 116 therebetween on base 114 of center section 110. Retainer elements 118 further include a plurality of gel retaining elements 126, which serve to affix air freshener element 116 in position, (allowing air to circulate through vents 119 and over air freshener element 116 and for emitted deodorizers to be emitted into the surrounding air, for example). Vents 119 are shown in FIGS.

4 and 6 as being in a pattern of circles and arcuate shapes, but may be arranged in any of a number of patterns and shapes.

The side section 112 includes a base 128, an air freshener element 116, a retainer element 118, an inner insert 130 and an outer insert 132. Base 128 includes a back wall 134, an upstanding wall 136 attached to back wall 134, a plurality of pegs 138 attached to back wall 134, and a channel 140. Back wall 134 and upstanding wall 136 together house therein an air freshener element 116 and retainer element 118. When side section 112 closes relative to center section 110, upstanding wall 136 of side section 112 is positioned radially to the outside of base 114 of center section 110, as illustrated in FIG. 6. This relative positioning when the side sections 112 are closed relative to center section 110 effectively seals air freshener elements 116 within the surrounding bases 114, 128 of center section 110 and side sections 112, thereby preserving air freshener elements 116. Air freshener element 116 in side section 112 is structurally substantially the same as air freshener element 116 in center section 110. In side section 112, air freshener element 116 is sandwiched between the back wall 134 of base 128 and retainer element 118 of side section 112. Air freshener element 116 includes a plurality of valleys 122 positioned adjacent pegs 138 of back wall 134. The retainer element of the side section is also structurally substantially the same as that of the center section. Retainer element 118 of side section 112 includes mounting through-holes 124 for mounting to pegs 138 attached to back wall 134 and also includes vents 119. Retainer element 118 of side section 112 is configured, for example, to form an interference fit with pegs 138 and can thereby snap onto these pegs. Inner insert 130 and outer insert 132 can be substantially identical to one another structurally, but can appear different aesthetically. The two inserts, 130, 132 can provide the user of the foldable air freshener system 100 with a plurality of aesthetically pleasing options in a convenient location, the inserts 130, 132 being able to be withdrawn and re-inserted in a different order to suit the desires of the user (that is, the inner insert can become the outer insert, and vice versa). Each of the inner 130 and outer 132 inserts are positioned on the opposite side of back wall 134 than air freshener element 116. The inner 130 and outer 132 inserts are slid into channel 140 formed on base 128 and are held therein by the channel 140 and retention pegs 138 on base 128. A tab 142 on inserts 130, 132 between retention pegs 138 is used to lift inserts 130, 132 over retention pegs 138 on base 128. Further base 128 of side section 112 includes a window 144 through which the inner insert 130 can be seen.

Each of the side sections 112 are pivotally connected to the center section 110 so that one or both of the side sections can be in an open position. The base 114 of the center section 110 includes two side walls 115. Each side wall 115 includes two outwardly mounted hinge pegs 146 and two interiorly mounted, outwardly projecting bars 148. The base 128 of a respective side section 112 includes two brackets 148 each including a hinge hole 150 and an interiorly mounted projection 152 (shown in FIG. 6). Each of the hinge holes 150 of the bracket 148 mounts to one of the hinge pegs 146 so that a pivotal connection can be established thereby. When the side section 112 is in the closed position, the projection 152 on the inside of the bracket 148 of the base 128 of the side section 112 abuts the projecting bar 148 on the inside of the side wall 15 of the base 114 of the center section 110; in this way, the projection 152 of the side section and the projecting bar 148 of the center section form a friction fit to gently lock the side section 112 to the center section 110 and also to provide a tactile feel that the side section 112 has reached the closed position. In this way, the side sections 112 can snap closed. A retention peg 154 is mounted on the outside of each side section 112, which retains air freshener system 100 in the closed position.

Each of the bases 114, 128 and the retainer elements 118 of the center 110 and side sections 112 can be formed, for example (and not by way of limitation), by a molding operation. For example, these structures can be made of a polymer material (which can be thermoplastic polymer or thermoset polymer) and can be formed by injection molding or reaction injection molding. The inner 130 and outer 132 inserts can be similarly formed or can be a paper product or another suitable material.

During assembly, the air freshener element 116 of the center section 110 can be positioned on the prongs 120 by way of the valleys 122 and then the retainer elements 118 of the center section 110 can be mounted on either side of the air freshener element 116 on these prongs 120 by way of the mounting through-holes 124, the retainer elements 118 snapping to and thereby being securely attached to these prongs 120. Similarly, regarding each of the side sections 112, the air freshener element 116 can be positioned on the back wall 134, the prongs 138 of the back wall 134 resting in the valleys 122 of the air freshener element 116. A retainer element 118 can be secured to these prongs 138 of the back wall 134 by way of the mounting through-holes 124 of the retainer element 118, the retainer elements 118 snapping to and thereby being securely attached to these prongs 138. The inserts 130, 132 can be slid into the channels 140 of the side sections 112 in the order desired. One or more side sections 112 can be opened or closed.

While this invention has been described with respect to at least one embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. An air freshener system, comprising:
  a roll paper assembly; and
  at least one air freshener assembly coupled with said roll paper assembly, said air freshener assembly including an integrated air freshener element in the form of a single, continuous gel component, said at least one air freshener assembly further including an inner cage and a cover, said gel component being positioned between said inner cage and said cover, said inner cage including a plurality of locking projections projecting radially inwardly from an inner upstanding wall and said cover having a plurality of radial inner openings, said plurality of locking projections of said inner cage configured to seat within said radial inner openings of said cover to form a snap fit.

2. The air freshener system according to claim 1, wherein said single, continuous gel component is a gel ring.

3. The air freshener system according to claim 1, wherein said roll paper assembly includes a roll core formed as a tubular element.

4. The air freshener system according to claim 3, wherein said air freshener assembly is configured to form an interference fit with an end of said roll core.

5. The air freshener system according to claim 1, wherein said inner cage includes a neck formed as a substantially cylindrical element configured for positioning within said roll core and a tray coupled with said neck.

6. The air freshener system according to claim 5, said tray including a base wall, an outer upstanding wall and said inner upstanding wall, wherein said base wall, said outer upstanding wall and said inner upstanding wall form a well in which said gel component is positioned.

7. The air freshener system according to claim 6, said tray further comprising a plurality of pegs positioned on said base wall and projecting in a direction towards said gel component and said cover.

8. The air freshener system according to claim 5, said tray defining a plurality of vents near an outer radius of said tray, said vents being configured to allow air to circulate within said inner cage and said cover and to pass at least one of over and through said gel component.

9. An air freshener system, comprising:
an inner cage including a tray coupled with a neck formed as a substantially cylindrical element configured for positioning within a longitudinal end of a roll core of a paper roll;
a cover coupled with said inner cage and including a base wall; and
a single, continuous gel component formed as a gel ring positioned within a well between said inner cage and said cover, said base wall of said cover including a plurality of vents, pegs and spacing walls configured to allow air to flow across or through said air freshener element.

10. The air freshener system according to claim 9, wherein said cover includes an inner wall positioned on an inner radius of said base wall, said inner wall projecting axially and together with said base wall forming a plurality of openings.

11. The air freshener system according to claim 10, said inner cage having a plurality of locking projections, said cover and said inner cage being attached to one another when said locking projections of said inner cage snap-fit into corresponding said plurality of openings.

12. An air freshener system, comprising:
a roll paper assembly; and
at least one air freshener assembly coupled with said roll paper assembly, said air freshener assembly including an integrated air freshener element in the form of a single, continuous gel component, said at least one air freshener assembly further including an inner cage and a cover, said gel component being positioned between said inner cage and said cover, said inner cage including a neck formed as a substantially cylindrical element configured for positioning within said roll core and a tray coupled with said neck, said tray defining a plurality of vents near an outer radius of said tray, said vents being configured to allow air to circulate within said inner cage and said cover and to pass at least one of over and through said gel ring, said tray further comprising a plurality of barbs spaced circumferentially about said tray and projecting radially outwardly and curving in one of a clockwise direction and a counter-clockwise direction.

* * * * *